US008556869B2

(12) United States Patent
Simon

(10) Patent No.: US 8,556,869 B2
(45) Date of Patent: Oct. 15, 2013

(54) IV FLOW RATE REGULATOR

(76) Inventor: Michael G. Simon, Del Mar, CA (US)

( * ) Notice: Subject to any disclaimer, the term of this patent is extended or adjusted under 35 U.S.C. 154(b) by 500 days.

(21) Appl. No.: 12/322,477

(22) Filed: Feb. 3, 2009

(65) Prior Publication Data

US 2010/0198167 A1 Aug. 5, 2010

(51) Int. Cl.
*A61M 5/00* (2006.01)

(52) U.S. Cl.
USPC .......... 604/248

(58) Field of Classification Search
USPC ........ 604/246–249, 255, 256, 288.03; 138/43
See application file for complete search history.

(56) References Cited

U.S. PATENT DOCUMENTS

| | | | |
|---|---|---|---|
| 3,207,641 | A | 9/1965 | Simko, Jr. et al. |
| 3,532,126 | A | 10/1970 | Boothe |
| 3,620,500 | A | 11/1971 | Santomieri |
| 3,656,138 | A | 4/1972 | Hamma |
| 3,785,378 | A | 1/1974 | Stewart |
| 3,806,086 | A | 4/1974 | Cloyd |
| 3,841,354 | A | 10/1974 | McDonnell |
| 3,868,973 | A | 3/1975 | Bierman et al. |
| 3,957,082 | A | 5/1976 | Fuson et al. |
| 4,079,737 | A | 3/1978 | Miller |
| 4,146,055 | A | 3/1979 | Ryder et al. |
| 4,300,552 | A | 11/1981 | Cannon |
| 4,361,147 | A | 11/1982 | Aslanian et al. |
| 4,384,680 | A | 5/1983 | Mehoudar |
| 4,474,574 | A | 10/1984 | Wolfe et al. |
| 4,504,263 | A | 3/1985 | Steuer et al. |
| 4,515,588 | A | 5/1985 | Amendolia |
| 4,533,348 | A | 8/1985 | Wolfe et al. |
| 4,581,014 | A | 4/1986 | Millerd et al. |
| 4,589,872 | A | 5/1986 | Bellin et al. |
| 4,593,717 | A | 6/1986 | Levasseur |
| 4,604,093 | A | 8/1986 | Brown |
| 4,613,325 | A | 9/1986 | Abrams |
| 4,634,434 | A | 1/1987 | Marino, Jr. et al. |
| 4,722,732 | A | 2/1988 | Martin |
| 4,738,665 | A | 4/1988 | Shepard |
| 4,769,012 | A | 9/1988 | Quang et al. |
| 4,789,000 | A | 12/1988 | Aslanian |
| 4,802,506 | A | 2/1989 | Aslanian |
| 4,807,660 | A | 2/1989 | Aslanian |
| 4,822,344 | A | 4/1989 | O'Boyle |
| 4,874,386 | A | 10/1989 | O'Boyle |
| 4,917,687 | A | 4/1990 | O'Boyle |
| 4,925,451 | A | 5/1990 | Amendolia |
| 4,947,856 | A | 8/1990 | Beard |
| 5,005,604 | A | 4/1991 | Aslanian |
| 5,009,251 | A | 4/1991 | Pike et al. |
| 5,014,750 | A | 5/1991 | Winchell et al. |
| 5,033,714 | A | 7/1991 | Winchell et al. |
| D319,506 | S | 8/1991 | Lal et al. |

(Continued)

OTHER PUBLICATIONS

3M Health Care brochure, "3M IV Flow Regulator Sets" (1993), 4 pages.

(Continued)

*Primary Examiner* — Kami A Bosworth
(74) *Attorney, Agent, or Firm* — Kinney & Lange, P.A.

(57) ABSTRACT

An IV flow regulator includes a housing, a flow control disk, a screw, and a dial. The flow control disk establishes a rate of flow through the housing. The flow rate regulator further includes alignment features allowing for high volume manufacturing while also being assembled into an accurate and reliable flow rate regulator.

10 Claims, 8 Drawing Sheets

70 84 78 30 66 32 28 34 64 26 69 36 24 46 48 38

(56) References Cited

U.S. PATENT DOCUMENTS

| | | | | |
|---|---|---|---|---|
| 5,113,904 | A | 5/1992 | Aslanian et al. | |
| 5,176,360 | A | 1/1993 | Winchell et al. | |
| 5,190,527 | A | 3/1993 | Hamilton et al. | |
| 5,234,413 | A | 8/1993 | Wonder et al. | |
| 5,240,035 | A | 8/1993 | Aslanian et al. | |
| 5,241,985 | A | 9/1993 | Faust et al. | |
| 5,445,622 | A | 8/1995 | Brown | |
| 5,449,350 | A * | 9/1995 | Lasaitis et al. | 604/246 |
| 5,499,968 | A | 3/1996 | Milijasevic | |
| 5,520,661 | A | 5/1996 | Lal et al. | |
| 5,730,730 | A | 3/1998 | Darling, Jr. | |
| 6,213,986 | B1 | 4/2001 | Darling, Jr. | |
| 6,290,681 | B1 | 9/2001 | Brown | |
| 6,709,417 | B1 | 3/2004 | Houle et al. | |
| 2003/0135164 | A1 | 7/2003 | Simon | |
| 2005/0065480 | A1 | 3/2005 | Lee et al. | |
| 2005/0131335 | A1 | 6/2005 | Drott et al. | |
| 2005/0197631 | A1 | 9/2005 | Schinazi et al. | |
| 2006/0135914 | A1 * | 6/2006 | Chu et al. | 604/248 |
| 2006/0229572 | A1 * | 10/2006 | Lopez | 604/256 |
| 2008/0009809 | A1 * | 1/2008 | Guala | 604/246 |

OTHER PUBLICATIONS

PCT International Search Report and Written Opinion of the International Searching Authority, Sep. 28, 2010, 9 pages.

* cited by examiner 14
10

16
12
22
18
20

12
30
32
28
34
26
36
24

IV FLOW RATE REGULATOR

BACKGROUND

Fluids and drugs are frequently administered to patients by intravenous infusion, also known as IV therapy. For IV therapy administration, a bag of IV solution is usually hung above a patient. Gravity pulls the IV solution downwards through a flexible line of delivery tubing to a venipuncture site on the patient, often in the forearm, wrist, or hand. To control the rate at which the IV solution is delivered to the patient, a pinch valve or roller clamp can be included on the outer surface of the tubing. Pinch valves and roller clamps compress the tubing to progressively restrict the flow of the IV solution reaching the patient's vein.

Even after a particular IV solution delivery rate is set with a pinch valve or roller clamp, substantial deviations in the flow rate can be observed. For example, as IV therapy progresses, the amount of IV solution remaining within the IV bag will be reduced. Along with this reduction in volume, the head pressure acting on the remaining IV solution is reduced and therefore, flow rate slows. Unwanted changes in flow rate can also be caused by changes in elevation of the IV bag or simple movement of a patient's limb. Indeed, Bernoulli's principle teaches that the total energy at a given point in a fluid is the energy associated with the movement of the fluid, plus energy from pressure in the fluid, plus energy from the height of the fluid relative to an arbitrary datum. Working knowledge of Bernoulli's principle, however, does not lead to a perfect pressure compensating flow rate controlling device. Pressure head variations are unpredictable and remain difficult to manage in IV therapy administration.

SUMMARY

An embodiment of the present invention is an IV flow rate regulator having at least one alignment element for ensuring coaxial alignment of IV flow rate regulator components. The IV flow rate regulator components include a housing having an inlet for receiving liquid, an outlet for discharging liquid and a metering port located between the inlet and the outlet. A flow control disk is located within the housing above the metering port. A screw extends into the housing to cooperate with the flow control disk. A dial is connected to the screw for rotating the screw to depress the flow control disk and thereby establish a flow rate at the metering port. At least one alignment element coaxially aligns at least one of the housing, the screw, or the dial along the central axis of the metering port.

Another embodiment of the present invention is an IV flow rate regulator having a mating attachment between the screw and the dial. The IV flow rate regulator includes a housing having an inlet for receiving liquid, an outlet for discharging liquid and a metering port located between the inlet and the outlet. A flow control disk is located within the housing above the metering port. A screw has a cavity and extends into the housing to cooperate with the flow control disk. A dial has a stem received by and mating with the screw cavity such that the dial and the screw are coaxially aligned with one another. The dial rotates the screw to depress the flow control disk and establish a rate of flow at the metering port.

Yet another embodiment of the present invention is an IV flow rate regulator having at least one crush feature for coaxially aligning IV flow rate regulator components. The IV flow rate regulator components include a housing having an upper housing section with a bore, a middle housing section with an inlet for receiving liquid and a metering port and a lower housing section with an outlet for discharging liquid. A flow control disk is located between the middle housing and the upper housing centered above the metering port. A screw extends through the bore to cooperate with the flow control disk. A dial rotates the screw to depress the flow control disk and establish a flow rate at the metering port. At least one crush feature located on at least one of the upper housing, the middle housing, the lower housing, and the screw to coaxially align the IV flow control regulator about a central axis defined by the metering port.

DETAILED DESCRIPTION

Precise control over flow rate during administration of IV therapy requires use of a flow regulating device that compensates for changes in fluid pressure. U.S. Pat. No. 7,361,165, which is hereby incorporated by reference, discloses an IV flow rate regulator having a control membrane for maintaining an essentially constant rate of flow in a gravity infusion system. Nevertheless, there exists a need for a reliable and accurate IV flow regulator capable of high volume robust manufacturing.

Figure 1:
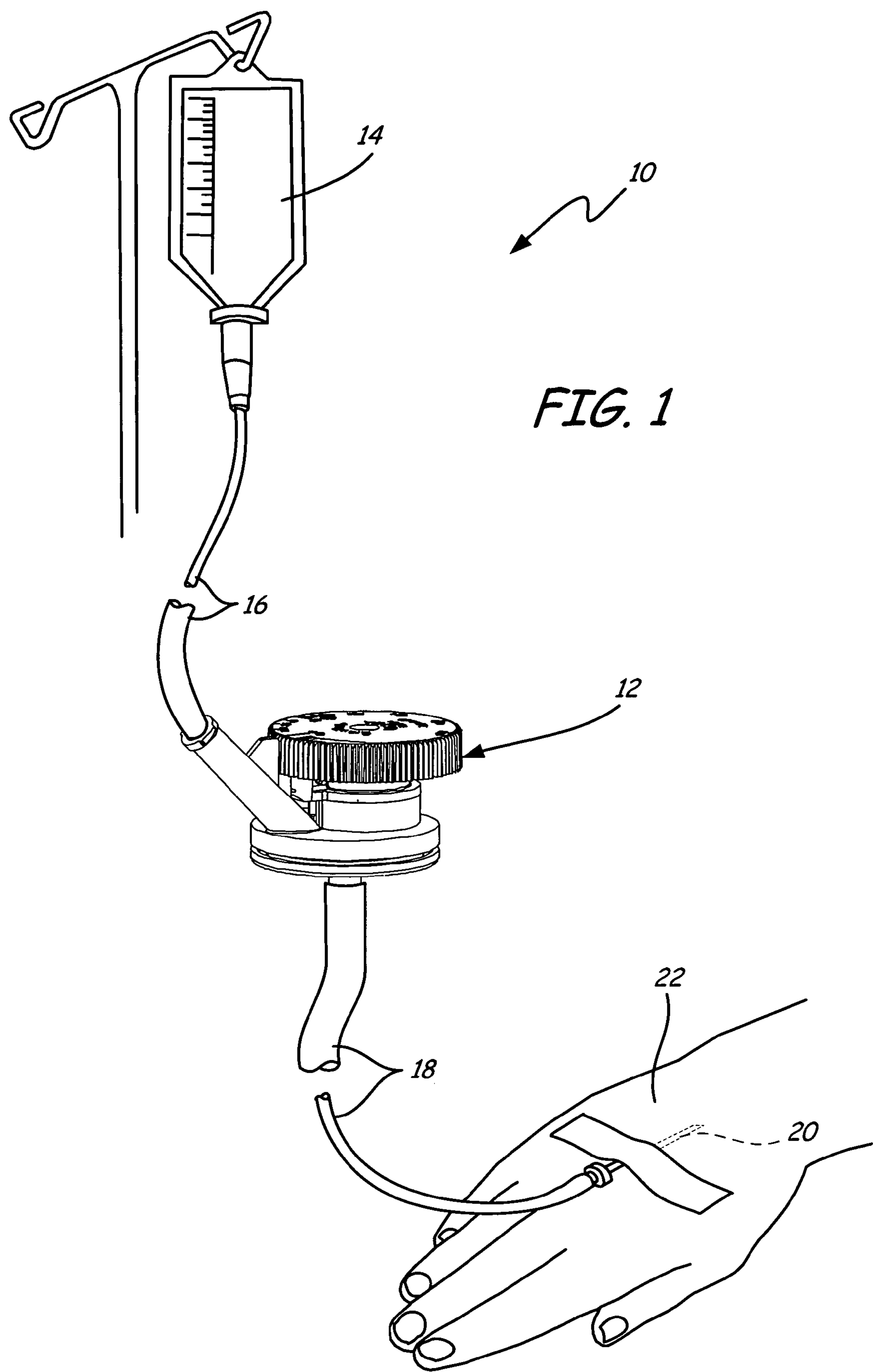
FIG. 1 is a schematic view of an IV therapy administration system including a flow rate regulator in accordance with the present invention.

FIG. 1 is a schematic view of IV therapy administration system 10 including flow rate regulator 12 in accordance with the present invention. Depicted in FIG. 1 are the components of IV therapy administration system 10: flow rate regulator 12, IV bag 14, upper tubing 16, lower tubing 18, venipuncture site 20, and patient 22. Flow rate regulator 12 compensates for variations in the head pressure of IV solution in IV therapy administration system 10.

Flow rate regulator 12 is located between IV bag 14 and venipuncture site 20. Fluidly connecting flow rate regulator 12 to IV bag 14 is flexible upper tubing 16. Similarly, flexible lower tubing 18 connects flow rate regulator 12 to venipuncture site 20 on patient 22. Venipuncture site 20 provides direct access to patient's 22 circulatory system via a needle or catheter inserted into a peripheral vein. To administer the contents of IV bag 14 to patient 22, IV bag 14 is hung above patient 22 with flow rate regulator 12 positioned between IV bag 14 and venipuncture site 20.

IV therapy administration system 10 uses gravity to pull an IV solution downwardly out of IV bag 14 through upper tubing 16 to flow rate regulator 12 through lower tubing 18 and into venipuncture site 20 on patient 22. In gravity IV therapy administration systems 10, flow regulator 12 uses fluid head pressure in IV bag 14 to overcome the venous back pressure of patient 22. As IV therapy progresses, however, the volume of solution within IV bag 14 is reduced. The reduced volume changes head pressure in the IV administration system 10, thereby slowing the rate at which solution is delivered to venipuncture site 20. Flow rate regulator 12 is configured to compensate for such variations in fluid pressure and maintain a predetermined flow rate.

Figure 2:
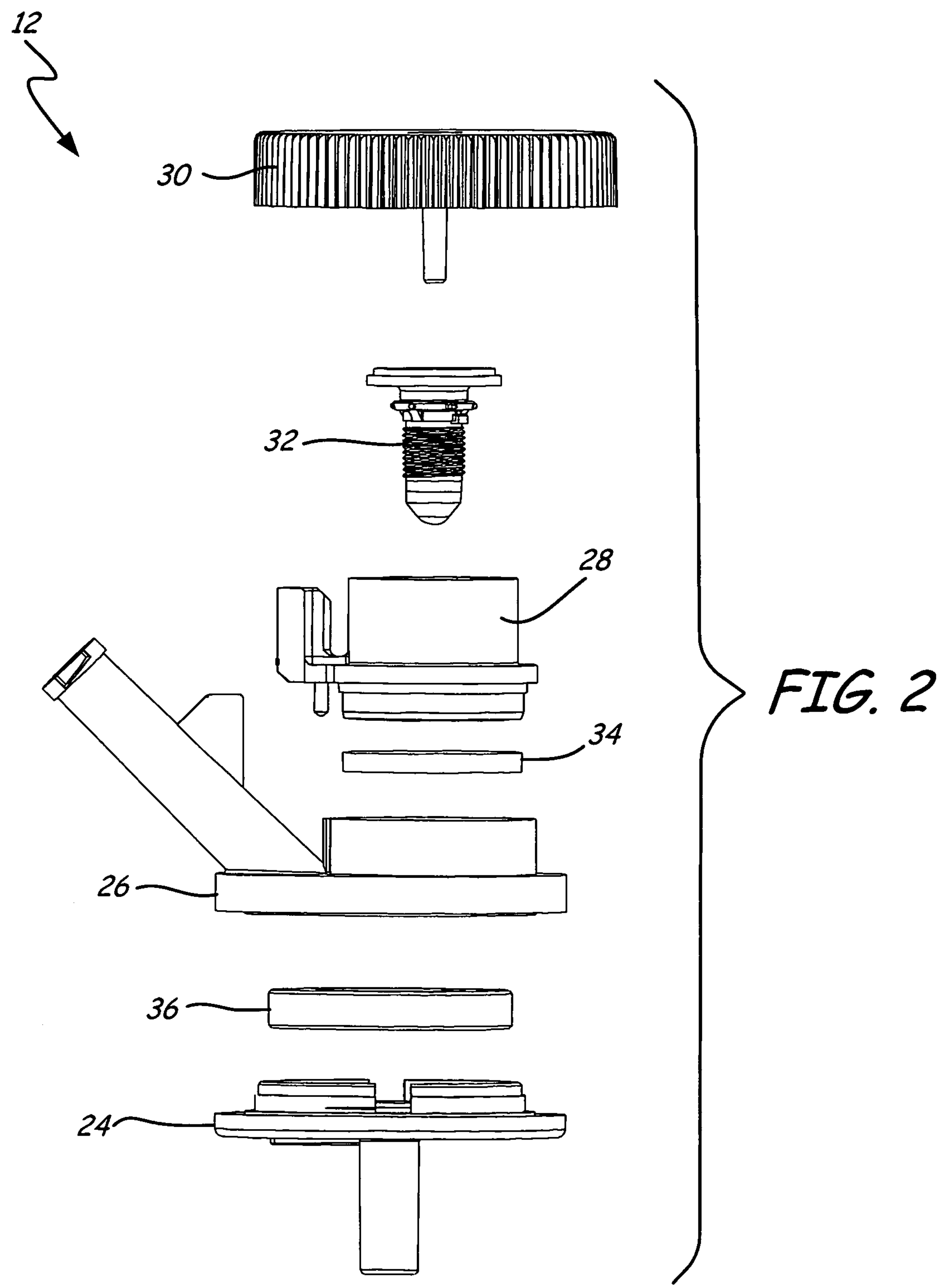
FIG. 2 is an exploded side view of the flow rate regulator from FIG. 1.

FIG. 2 is an exploded side view of flow rate regulator 12 from FIG. 1. Depicted in FIG. 2 are the components of flow rate regulator 12: lower housing 24, middle housing 26, upper housing 28, dial 30, screw 32, flow control disk 34, and flexible membrane 36. The components of flow rate regulator 12 are assembled to control flow rate, as well as compensate for changes in fluid pressure, within IV administration system 10.

Flow rate regulator 12 is constructed from lower housing 24, middle housing 26, and upper housing 28. Lower housing 24, middle housing 26, and upper housing 28 can be formed by injection molding of a suitable medical grade plastic material such as polypropylene. Just as the names indicate, lower housing 24 is located beneath and attached to middle housing 26, which is located beneath and attached to upper housing 28. Orifices fluidly connect lower housing 42 with middle housing 26 and upper housing 28. Located above upper housing 26 is dial 30. Dial 30 mates securely with screw 32, which sits within upper housing 28. In between upper housing 28 and middle housing 26, and sitting within middle housing 26, is flow control disk 34. Similarly, located between middle housing 26 and lower housing 24, and sitting within lower housing 24, is flexible membrane 36. Flow control disk 34 and flexible membrane 36 can be formed by compression molding of a suitable medical grade material elastomer, such as silicone rubber. So assembled, the components of flow regulator 12 function to both set and maintain the flow rate of an IV solution in IV therapy administration system 10.

IV solution enters flow rate regulator 12 through middle housing 26 and encounters flow control disk 34. If dial 30 and screw 32 are in an "on" or "full open" position, then little to no pressure is placed on flow control disk 34 and therefore, fluid passes by flow control disk 34 unrestricted. If, however, dial 30 is used to progress screw 32 downwardly into threads of upper housing 28, the tip of screw 32 will exert pressure on flow control disk 34. Under such mechanical pressure, flow control disk 34 deforms and takes up additional space within middle housing 26 thereby slowing the movement of fluid through middle housing 26. Taken to the extreme, dial can turn screw 32 to an "off" position, where little to no fluid is capable of passing through middle housing 26. Fluid that is allowed through an orifice of middle housing 26 encounters flexible membrane 36 located in lower housing 24. A top surface of flexible membrane 36 is at essentially the same pressure as IV fluid within IV bag 14, whereas a bottom surface of flexible membrane 36 is at essentially the same pressure as venipuncture site 20. If pressure exerted on the top surface of flexible membrane 36 is reduced, flexible membrane 36 will flex away from lower housing 24 effectively increasing the size of the passageway and therefore, the rate of fluid flow. The converse is also true such that an increase in top surface pressure results in flexible membrane 36 flexing toward lower housing 24 thereby decreasing rate of fluid flow. Flexible membrane 36 flexes or oscillates to compensate for changes in fluid pressure thereby maintaining the flow rate set by use of dial 30 and screw 32 cooperating with flow control disk 34. The components of flow rate regulator 12 are discussed individually and in further detail below.

Lower Housing 24

Figure 3:
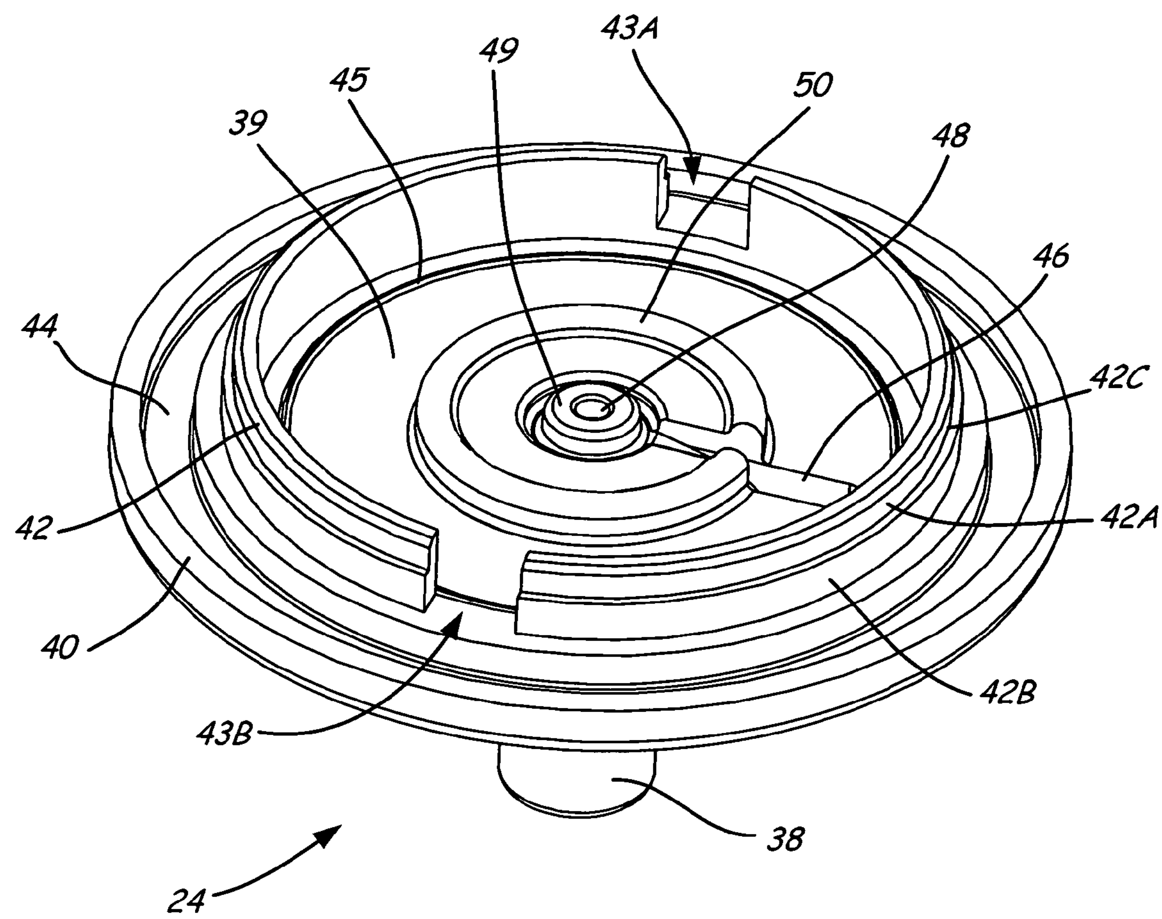
FIG. 3 is a top perspective view of the lower housing from FIG. 2.

FIG. 3 is a top perspective view of lower housing 24 from FIG. 2. Depicted in FIG. 3 are the components of lower housing 24: outlet port 38, top surface 39, rim 40, flange 42, notches 43, track 44, sealing ring 45, channel 46, lower orifice 48, port ring 49, and land 50. Lower housing 24 is configured to hold flexible membrane 36, which is responsible for accommodating changes in fluid pressure.

Extending downwardly from an approximate center of generally circular lower housing 24 is outlet port 38. In the depicted embodiment, outlet port 38 forms an approximately right angle with the bottom surface of lower housing 24, and is sized to receive medical tubing, such as lower tubing 18. The circumference of lower housing 24 is defined by rim 40, which protrudes upwardly from a top surface of lower housing 24. Within rim 40 and also extending upwardly from top surface 39 is flange 42. Flange 42 includes upper portion 42A, a lower portion 42B, and shoulder 42C located between upper portion 42A and lower portion 42B. Although flange 42 is mostly continuous and annular, one or more cut-outs or notches 43 can extend into flange 42. In the embodiment depicted, two notches 43A and 43B are shown. Between rim 40 and flange 42 is annular track 44, which also extends around the top surface of lower housing 24. Inside of, and immediately adjacent to flange 42, is sealing ring 45. Sealing ring 45, like track 44, is annular and continuous around top surface 39 of lower housing 24. In the embodiment depicted, sealing ring 45 has a height between approximately 0.005 and 0.015 inches (0.0127 and 0.0381 centimeters) and a width between approximately 0.015 and 0.025 inches (0.0381 and 0.0635 centimeters), although the invention is not so limited. Sealing ring 45 can assume any configuration capable of maintaining a proper seal with flexible membrane 36. Located within sealing ring 45 is radial channel 46 extending from a location near sealing ring 45 to centrally located lower orifice 48 and port ring 49. Lower orifice 48 leads fluid from channel 46 into outlet port 38 and therefore, out of flow rate regulator 12. Also within sealing ring 45 and extending around orifice 48 is land 50. Land 50 is substantially annular except for a small cut-out where channel 46 is connected to orifice 48 to allow for fluid connection.

Lower housing 24 is the lowermost portion of flow rate regulator 12. Outlet port 38 is the location where fluid is discharged from flow rate regulator 12, usually into lower tubing 18 for administration to patient 22. Upwardly extending rim 40, flange 42, notches 43, and track 44 are all configured to couple with corresponding mating parts depending downwardly from middle housing 26. Once so assembled, fluid exiting middle housing 26 arrives at channel 46 of lower housing 24 and is directed inwards toward lower orifice 48. Before reaching port ring 49 and lower orifice 48, fluid encounters flexible membrane 36, which rests centrally on top surface 39 of lower housing 24 within flange 42 to engage sealing ring 45. Sealing ring 45 functions to prevent fluid from leaking out of lower housing 24 and also secures flexible membrane 36 onto top surface 39 of lower housing 24. Flexible membrane 36 stretches across land 50 and flexes or oscillates to maintain the pressure differential between IV bag 14 and venipuncture site 20. So assembled, lower housing 24 contains flexible membrane 36, which compensates for changes in fluid pressure with IV therapy administration system 10.

Middle Housing 26

Figure 4A:
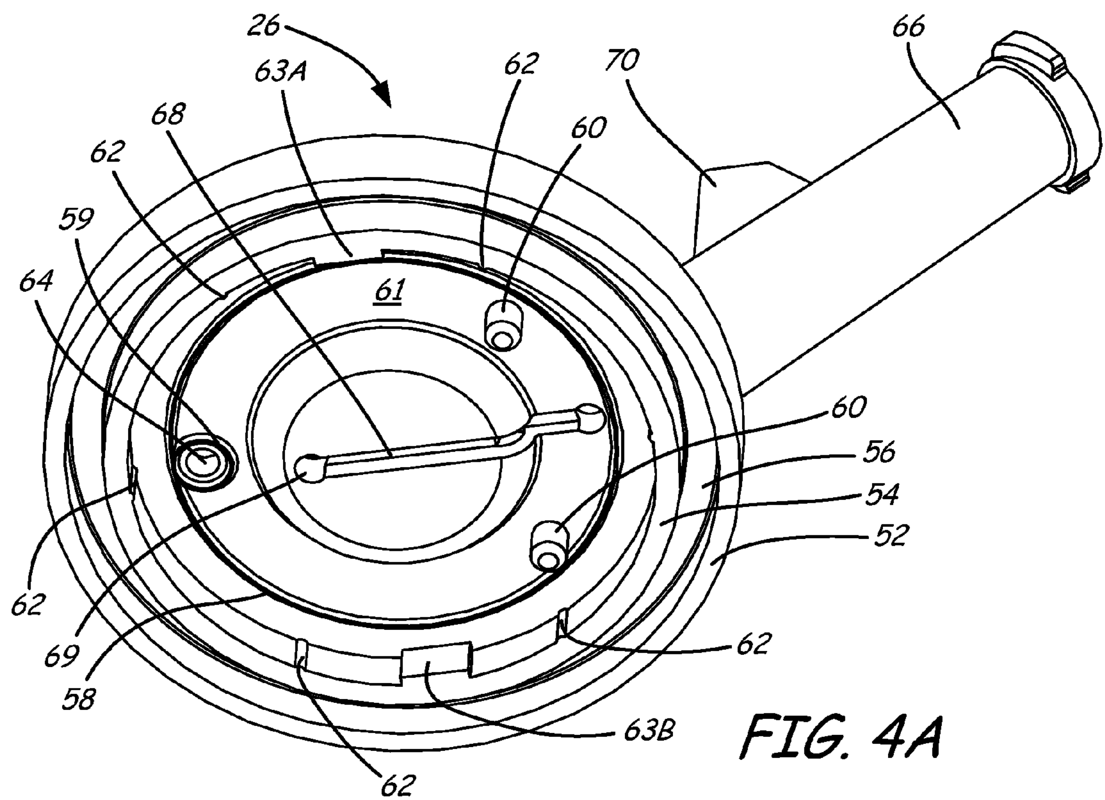
FIG. 4A is a bottom perspective view and FIG. 4B is a top perspective view of the middle housing from FIG. 2.
Figure 4B:
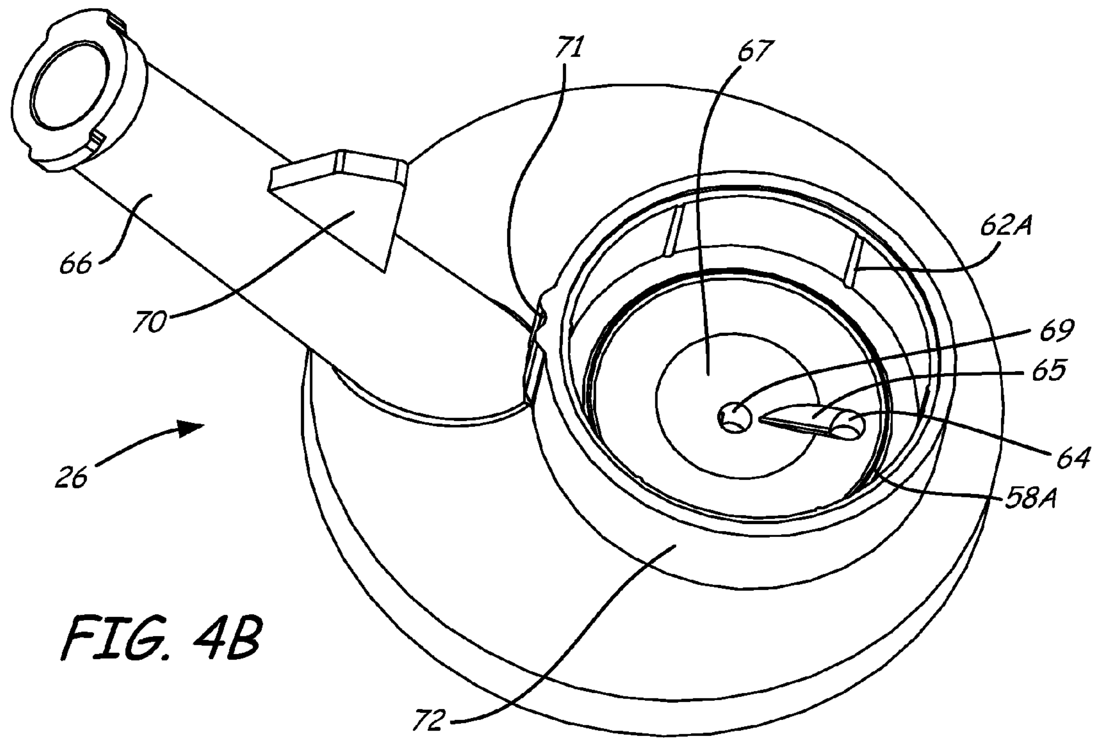

FIG. 4A is a bottom perspective view and FIG. 4B is a top perspective view of middle housing 26 from FIG. 2. Depicted in FIG. 4A are the components of middle housing 26 as seen from the bottom: outer lip 52, inner lip 54, track 56, sealing rings 58 and 59, locator pins 60, centering ribs 62, keys 63A and 63B, orifice 64, inlet 66, channel 68, metering port 69, and fin 70. Depicted in FIG. 4B are the components of middle housing 26 as seen from the top: sealing ring 58A, centering ribs 62A, orifice 64, V-Channel 65, inlet 66, circular concave funnel 67, metering port 69, fin 70, detent 71 and flange 72. An upper surface of middle housing 26 is configured to hold flow control disk 34, which cooperates with screw 32 and dial 30 to establish a rate of flow through flow rate regulator 12.

Extending downwardly from a bottom surface of middle housing 26 are outer lip 52 and inner lip 54. Both inner lip 54 and outer lip 52 are annular and continuous. Outer lip 52 depends from the periphery of middle housing 26, and inner lip 54 is located inside of outer lip 52 such that an annular track 56 is created between outer lip 52 and inner lip 54. Located inside of inner lip 54 is annular sealing ring 58, and located inside of sealing ring 58 are locator pins 60 and orifice 64. Extending around orifice 64 is sealing ring 59. Sealing rings 58 and 59 are similar in structure to sealing ring 45 described above in that they each have a height between approximately 0.005 and 0.015 inches (0.0127 and 0.0381 centimeters) and a width between approximately 0.015 and 0.025 inches (0.0381 and 0.0635 centimeters), although the invention is not so limited. Sealing rings 58 and 59 can assume any configuration capable of maintaining a proper seal with flexible membrane 36. In the embodiment depicted, two locator pins 60 extend downwardly from bottom surface 61 to mate with flexible membrane 36 and precisely align membrane 36 to middle housing 26. Channel 68 extends from inlet 66 along a bottom surface of middle housing 26 to metering port 69. Ribs 62 (protruding centrally from inner lip 54 at regular intervals), along with keys 63A and 63B, precisely align middle housing 26 to flexible membrane 36 and lower housing 24.

When flexible membrane 36 is resting on the top surface 39 of lower housing 24 within flange 42, inner lip 54 of middle housing 26 is configured to slide over flange 42 and encapsulate flexible membrane 36 between lower housing 24 and middle housing 26. More specifically, inner lip 54 of middle housing 26 rests on shoulder 42C of lower housing 24. Sealing rings 58 and 59 grip and thereby seal flexible membrane 36 to the bottom surface of middle housing 26. To further secure flexible membrane 36 into its predetermined location, locator pins 60 are received into holes located on a top peripheral surface of flexible membrane 36. Even further still, centering ribs 62 center inner lip 54 of middle housing 26 with respect to an outer of flange 42 from lower housing 24. Key 63A engages notch 43A and key 63B engages notch 43B to ensure proper rotational alignment of middle housing 26 and lower housing 24. Thus, inner lip 54, sealing rings 58 and 59, locator pins 60, centering ribs 62, and keys 63A, 63B all serve to center and coaxially align middle housing 26 with respect to lower housing 24 and flexible membrane 36.

Inlet 66 extends outwardly and upwardly from a top surface of middle housing 26 at an angle between approximately 45 and 90 degrees. In the embodiment depicted, inlet 66 is circular in cross-section and sized to be connectable to conventional medical tubing, such as upper tubing 16. Inlet 66 defines an inlet passage for receiving liquid that is fluidly connected to channel 68, which is fluidly connected to metering port 69. Leading into metering port 69 is circular concave funnel 67. Protruding from a top surface of inlet 66 is fin 70. Fin 70 is more or less shaped like a triangle, but has a flat on its top surface. As seen from the top, metering port 69 is surrounded by annular sealing ring 58A, which is surrounded by upwardly extending flange 72. Just like sealing ring 58, sealing ring 58A has a height between approximately 0.005 and 0.015 inches (0.0127 and 0.0381 centimeters) and a width between approximately 0.015 and 0.025 inches (0.0381 and 0.0635 centimeters), although the invention is not so limited. Sealing ring 58A can assume any configuration capable of maintaining a proper seal with flow control disk 34. Protruding centrally from an inside surface of flange 72 at regular intervals are ribs 62A to precisely align middle housing 26 to upper housing 28.

Inlet 66 is offset at an angle to allow for use of a large diameter dial 30. The flat top surface of fin 70 provides a location on inlet 66 to carry a fiduciary mark for cooperation with flow rate indicia located on a top surface of dial 30. Liquid received by inlet 66 flows downwardly through the inlet passageway into channel 68. At the other end of channel 68 is metering port 69, which may or may not be restricted by flow control disk 34. Flow control disk 34 rests inside of flange 72 above metering port 69, circular concave funnel 67, V-channel 65, orifice 64 and sealing ring 58A. If screw 32 and dial 30 are in a "full open" position, liquid will flow freely through channel 68, metering port 69, and orifice 64 into lower housing 24. When screw 32 is advanced downwardly by rotation of dial 30, however, pressure is exerted on flow control disk 34, which causes flow control disk 34 to deform slightly. The deformed flow control disk 34 limits the rate at which liquid flows through metering port 69 to orifice 64. Sealing ring 58A grips and thereby seals flow control disk 34 to middle housing 26. Centering ribs 62A within flange 72 are configured to center middle housing 26 with respect to upper housing 28 such that middle housing 26 is centered and coaxially aligned with flow control disk 34, the central axis of metering port 69, and upper housing 28.

Upper Housing 28

Figure 5A:
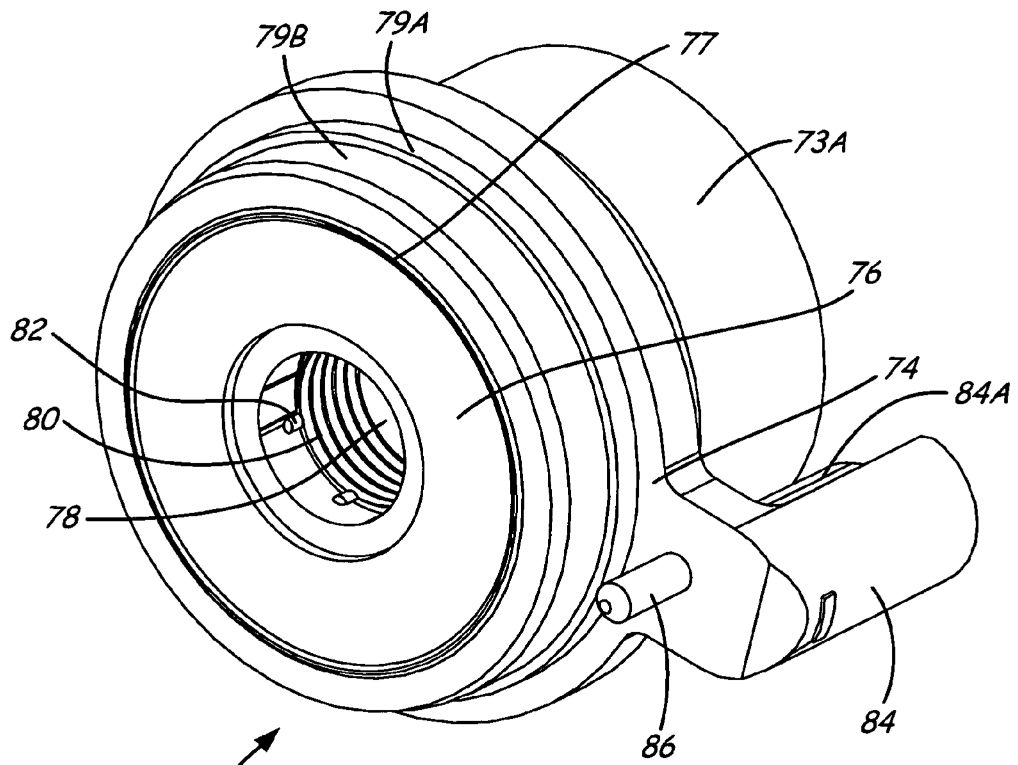
FIG. 5A is a bottom perspective view and FIG. 5B is a top perspective view of the upper housing from FIG. 2.
Figure 5B:
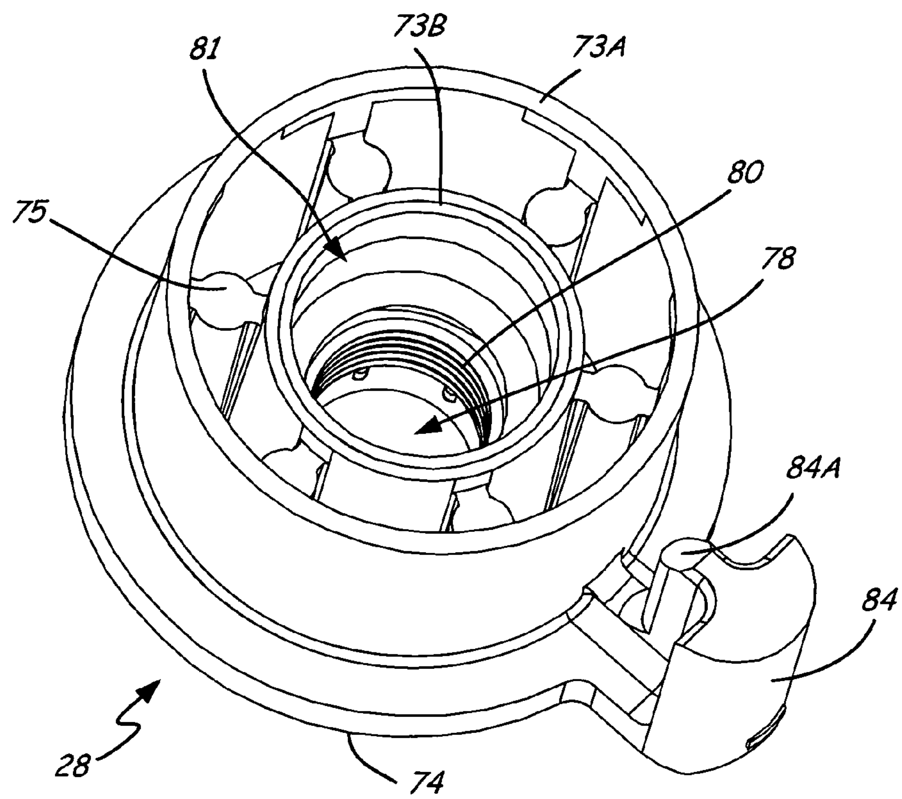

FIG. 5A is a bottom perspective view of upper housing 28 from FIG. 2, and FIG. 5B is a top view of upper housing 28. Depicted in FIGS. 5A and 5B are the components of upper housing 28: outer wall 73A, inner wall 73B, lower shoulder 74, inner supports 75, bottom surface 76, sealing ring 77, lower bore 78, step 79A, centering wall 79B, threads 80, upper bore 81, crush ribs 82, arm 84, and locating pin 86. Upper housing 28 is configured to couple with middle housing 26 while holding screw 32 adjacent to flow control disk 34.

Upper housing 28 has a generally cylindrical body defined by outer wall 73A. Inner wall 73B is located concentrically within outer wall 73A, and supports 75 are positioned at spaced locations between walls 73A and 73B. Inner wall 73B contains lower bore 78 and upper bore 81. Shoulder 74 is a raised surface extending around a circumference of outer wall 73A of upper housing 28. Shoulder 74 is located on an exterior surface of upper housing 28, but is adjacent and parallel to bottom surface 76. Extending from and around bottom surface 76 is sealing ring 77. Just like sealing ring 58A, sealing ring 77 has a height between approximately 0.005 and 0.015 inches (0.0127 and 0.0381 centimeters) and a width between approximately 0.015 and 0.025 inches (0.0381 and 0.0635 centimeters), although the invention is not so limited. Sealing ring 77 can assume any configuration capable of maintaining a proper seal with flow control disk 34. Extending through the center of upper housing 28 are lower bore 78 and upper bore 81. Located on an inside surface of lower bore 78 are screw threads 80. Also on an inside surface within lower bore 78, beneath screw threads 80 and closer to bottom surface 76, are crush ribs 82. Upper bore 81 has a larger diameter than lower bore 78, and is not threaded. Protruding outwardly and upwardly from one side of shoulder 74 is arm

84. Extending from a bottom surface of arm 84, in an opposite direction as arm 84, is locating pin 86.

When upper housing 28 is assembled into middle housing 26, step 79A of upper housing 28 rests on a top surface of flange 72 on middle housing 26. In this location, centering wall 79B slides within flange 72 to engage centering ribs 62A on the inside surface of flange 72. Just as the names indicate, centering ribs 62A of middle housing 26 and centering wall 79B of upper housing 28 cooperate to maintain concentricity between upper housing 28, control disk 34 and middle housing 26. So placed, bottom surface 76 of upper housing 28 is located directly above flow control disk 36, which is located directly above metering port 69. Sealing ring 77 engages top surface of flow control disk 36 to prevent fluid leaks. Lower bore 78 is internally threaded 80 to receive and engage threads located on an external surface of screw 32. As screw 32 is inserted into bore 78, crush ribs 82 crush away to secure screw 32 within bore 78 of upper housing 28. Crush ribs 82 assure that screw 32 is concentric, centered, and precisely aligned with respect to upper housing 28, control disk 34, circular concave funnel 67 and metering port 69. Arm 84 extends upwards to cooperate with stop 114 of dial 30 in establishing the off, or zero flow position for flow rate regulator 12. Locating pin 86 extends downwards along an outside surface of flange 74 to cooperate with detent 71 located on flange 72 on middle housing 26. When locating pin 86 cooperates with detent 71 on flange 72 of middle housing 26, rib 84A on arm 84 of upper housing 28 is precisely aligned with fin 70 on middle housing 26.

Screw 32

Figure 6A:
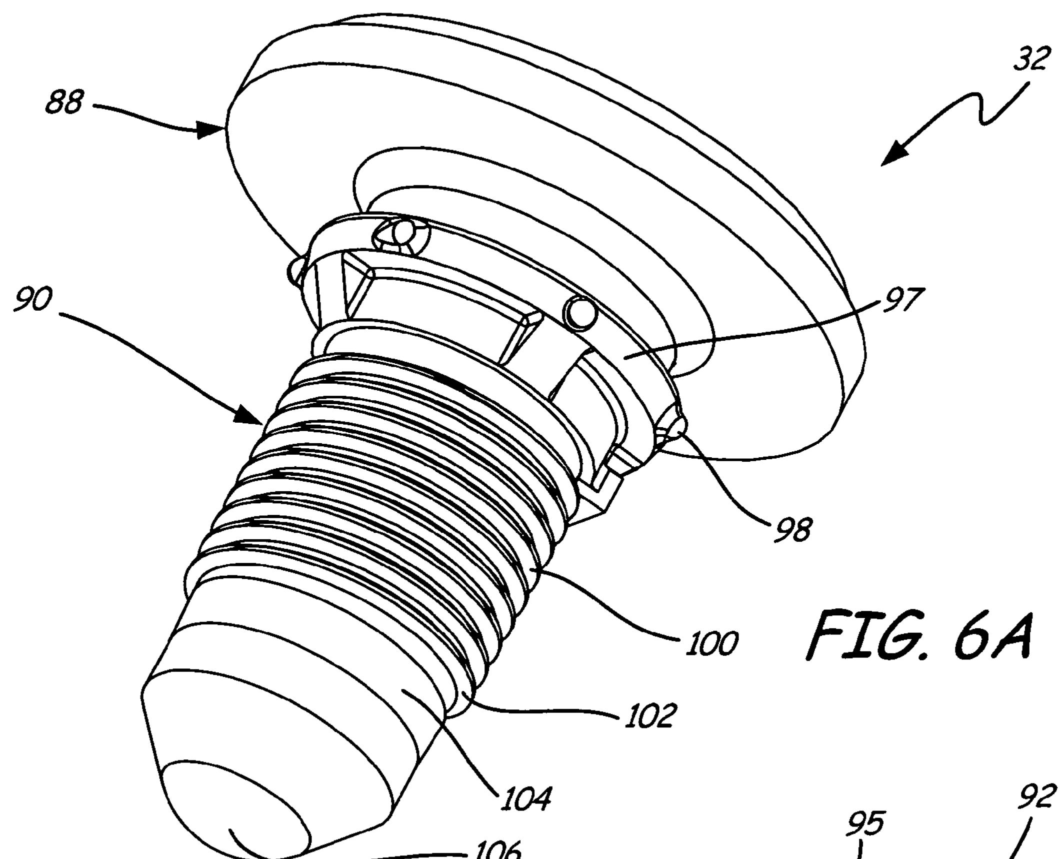
FIG. 6A is a bottom perspective view and FIG. 6B is a top perspective view of the screw from FIG. 2.
Figure 6B:
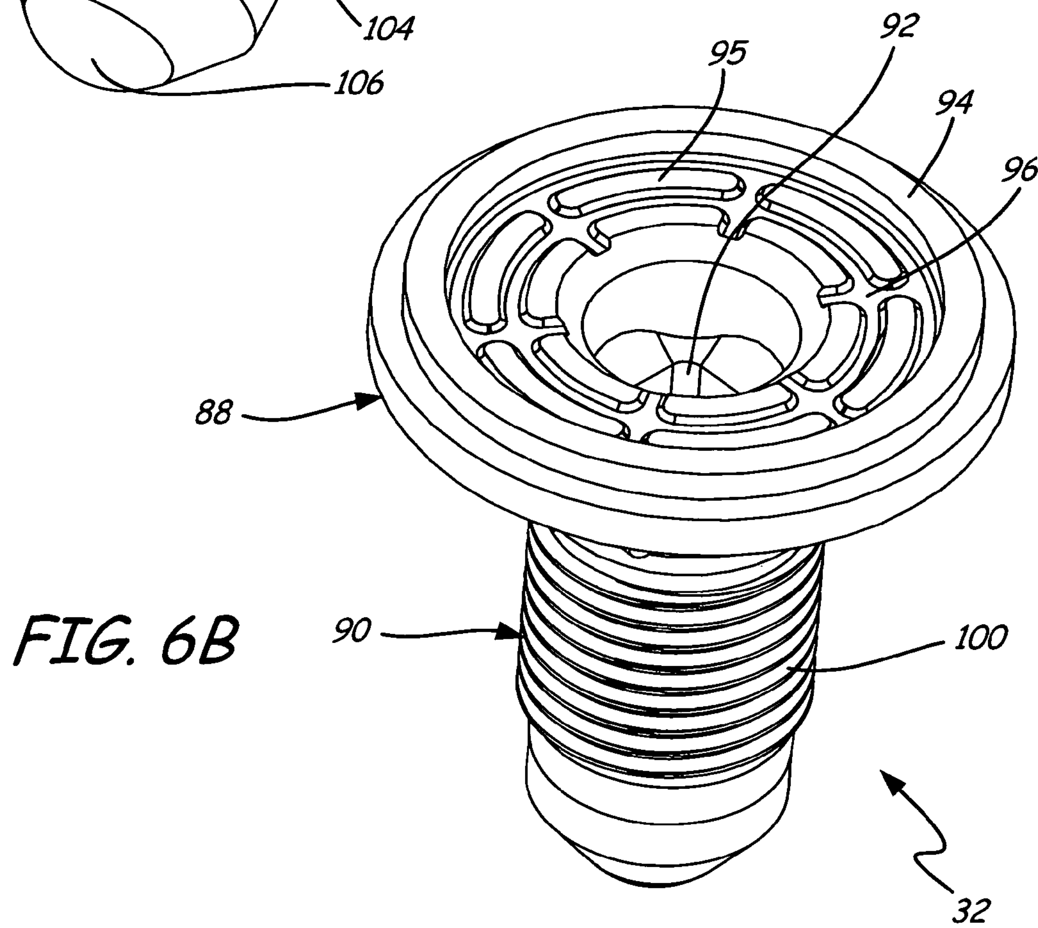

FIG. 6A is a bottom perspective view and FIG. 6B is a top perspective view of screw 32 from FIG. 2. Depicted in FIG. 6A are screw 32 components as viewed from the bottom: head 88, body 90, flange 97, crush bumps 98, threads 100, lead thread 102, taper 104, and tip 106. Depicted in FIG. 6B are screw 32 components as viewed from the top: head 88, body 90, cavity 92, retaining rib 94, flow channel pads 95, flow channels 96, and threads 100. Screw 32 is configured to couple with dial 30 and rotate within upper housing 28 to change the flow rate of flow rate regulator 12 by exerting force on flow control disk 34.

Screw 32 has a flat circular head 88, from which elongate body 90 extends. Beginning at head 88 and extending centrally into body 90 is cavity 92. In the embodiment depicted, cavity 92 extends substantially an entire length of body 90, is slightly tapered, and is square in cross-section. In other words, screw 32 is “cored out” such that body 90 contains cavity 92. Head 88 has retaining rib 94 extending upwardly from a top surface. Within retaining rib 94, but also located on the top surface of head 88 are flow channel pads 95 and flow channels 96. In the embodiment depicted, flow channel pads 95 form raised arcuate patterns that define flow channels 96 between retaining rib 94 and the opening to cavity 92. Crush bumps 98 protrude at regular intervals and at a defined radial distance from an outer surface of flange 97 adjacent to head 88 to create an interference with a slightly tapered inner surface of bore 78 of upper housing 28 during assembly. Beneath crush bumps 98 are screw threads 100, which surround the central portion of body 90. Lead screw thread 102 is the last of screw threads 100 such that it is located most remotely from crush bumps 98 and head 88. Directly beneath lead screw thread 102 on body 90 is taper 104. In other words, a diameter of body 90 is less at the bottom of taper 104, than a diameter of body 90 directly under screw threads 100. Lastly on body 90 and beneath taper 104 is screw tip 106. In the embodiment depicted, tip 106 is spherical or cone-shaped and is free of all sink or open knit lines. In the embodiment depicted, a radius of tip 106 is between approximately 0.071-0.075 inches (0.180-0.191 centimeters) to optimize interface with flow control disk 34.

During assembly of flow control regulator 12, crush bumps 98 on the outer surface of flange 97 engage upper bore 81 of upper housing 28 when screw 32 is advanced into upper housing 28 such that a line-to-line fit is created at the off or zero flow position when metering port 69 is closed off by control disk 34. Adhesive is then deposited into cavity 92 to adhere screw 32 and dial 30 together. Retaining rib 94 contains adhesive such that when stem 116 of dial 30 (shown in FIG. 7) fully engages cavity 92 of screw 32, the adhesive flows through flow channels 96 and becomes evenly distributed on head 88 without pouring down onto body 90 and threads 100. Head 88 provides a large surface area for adhesive distribution, which results in a robust bond with dial 90. Furthermore, taper 104 of screw 32 has a circumference designed to engage crush ribs 82 located on the inside of lower bore 78 of upper housing 28. As screw 32 is advanced into upper housing 28, the inside surface of upper bore 81 deforms crush bumps 98 located on flange 97 of screw 32, and taper 104 of screw 32 deforms crush ribs 82 located in lower bore 78 of upper housing 28. This coupling between screw 32 and upper bore 81 and lower bore 78 serves to precisely center and concentrically align screw 32 with upper housing 28. Lead screw thread 102 is angled to prevent cross threading of screw 32 within lower bore 78 of upper housing 28. Tip 106 has a shape and surface designed to optimize the flow rate settings obtained by screw 32 and dial 30 cooperating with flow control disk 34, circular concave funnel 67, metering port 69 and V-channel 65.

Dial 30

Figure 7:
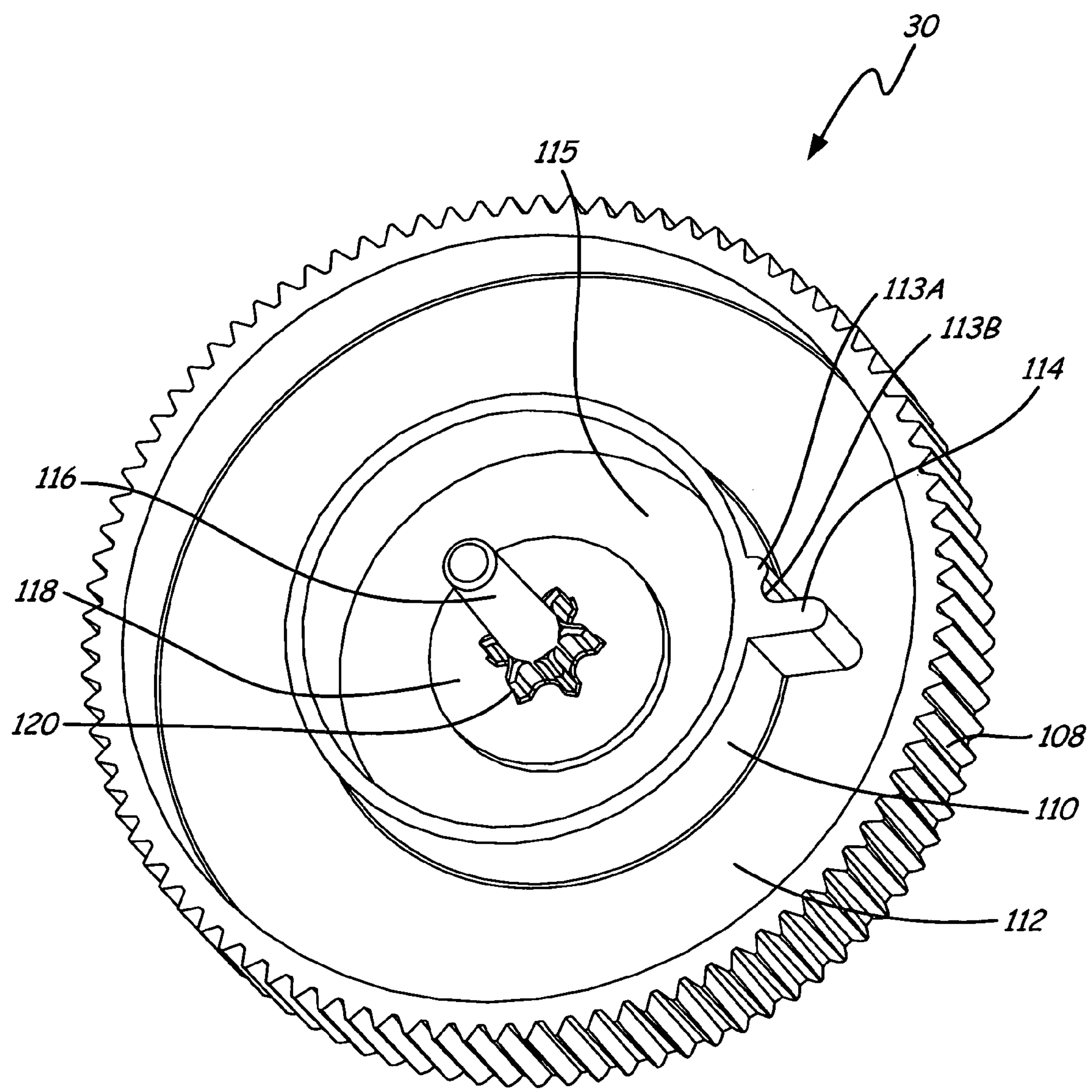
FIG. 7 is a bottom perspective view of the dial from FIG. 2.

FIG. 7 is a bottom perspective view of dial 30 from FIG. 2. Depicted in FIG. 7 are components of dial 30: serrated wall 108, hub 110, outer bottom surface 112, detent 113A, cradle 113B, stop 114, inner bottom surface 115, stem 116, pad 118, and ribs 120. Stem 116 of dial 30 is received by cavity 92 of screw 32 such that dial 30 and screw 32 are coupled together to adjust the flow rate of flow rate regulator 12.

Dial 30 is generally circular and has a diameter larger than a diameter of upper housing 28, but similar to a diameter taken from the largest part of middle housing 26 or lower housing 24. Extending downwards from the periphery of dial 30 is serrated wall 108. Serrated wall 108 is continuous around outside surface of dial 30. Inside of serrated wall 108, but also extending downwardly from dial 30 is hub 110. Located along a bottom surface 112 of dial 30 is outer serrated wall 108 and hub 110. Extending from hub 110 into outer bottom surface 112 is stop 114. In the embodiment depicted, stem 116 projects from pad 118 and is between approximately 0.25 and 0.75 inches from a bottom surface of dial and is approximately circular in cross-section. Attached to inner bottom surface 115 and surrounding centrally located stem 116, is circular pad 118. Extending around stem 116 at regular intervals in a location adjacent to pad 118 are radial projections or ribs 120. In other words, ribs 120 are provided at the junction of stem 116 and pad 118 on the bottom surface of dial 30.

Top surface of dial 30 is flat and carries indicia or markings corresponding to a plurality of flow rates for flow rate regulator 12. Serrated wall 108 provides a tactile surface for manipulation of dial 30 as it is rotated approximately 360° between a fully off position (screw 32 exerting maximal pressure on flow control disk 34) and a fully open position (screw 32 exerting minimal pressure on flow control disk 34). Detent 113A, cradle 113B, and, stop 114 define the off or zero flow position which is precisely aligned with fin 70 on middle housing 26. In the embodiment depicted, when rib 84A of arm 84 on upper housing 28 rests in cradle 113B, flow rate regulator 12 is in the "off" position. Stem 116 projects from dial 30 to mate with cavity 92 of screw 32. As described above, adhesive is introduced into cavity 92 to adhere screw 32 and dial 30 to one another. The long projection that defines stem 116 is received into adhesive-filled cavity 92 until pad 118 on the bottom surface of dial 30 engages flow channel pads 95 of screw 32; while, retaining rib 94 of screw 32 makes no contact with dial 30. Once so assembled, a robust bond forms between screw 32 and dial 30. Ribs 120 are configured to self-center dial 30 with respect to screw 32. Ribs 120 also serve to prevent relative rotation between dial 30 and screw 32 when assembled. So assembled, dial 30 and screw 32 are coaxially aligned above metering port 69 and thus, operate as one component functioning to set a flow rate for flow rate regulator 12.

Operation

Figure 8:
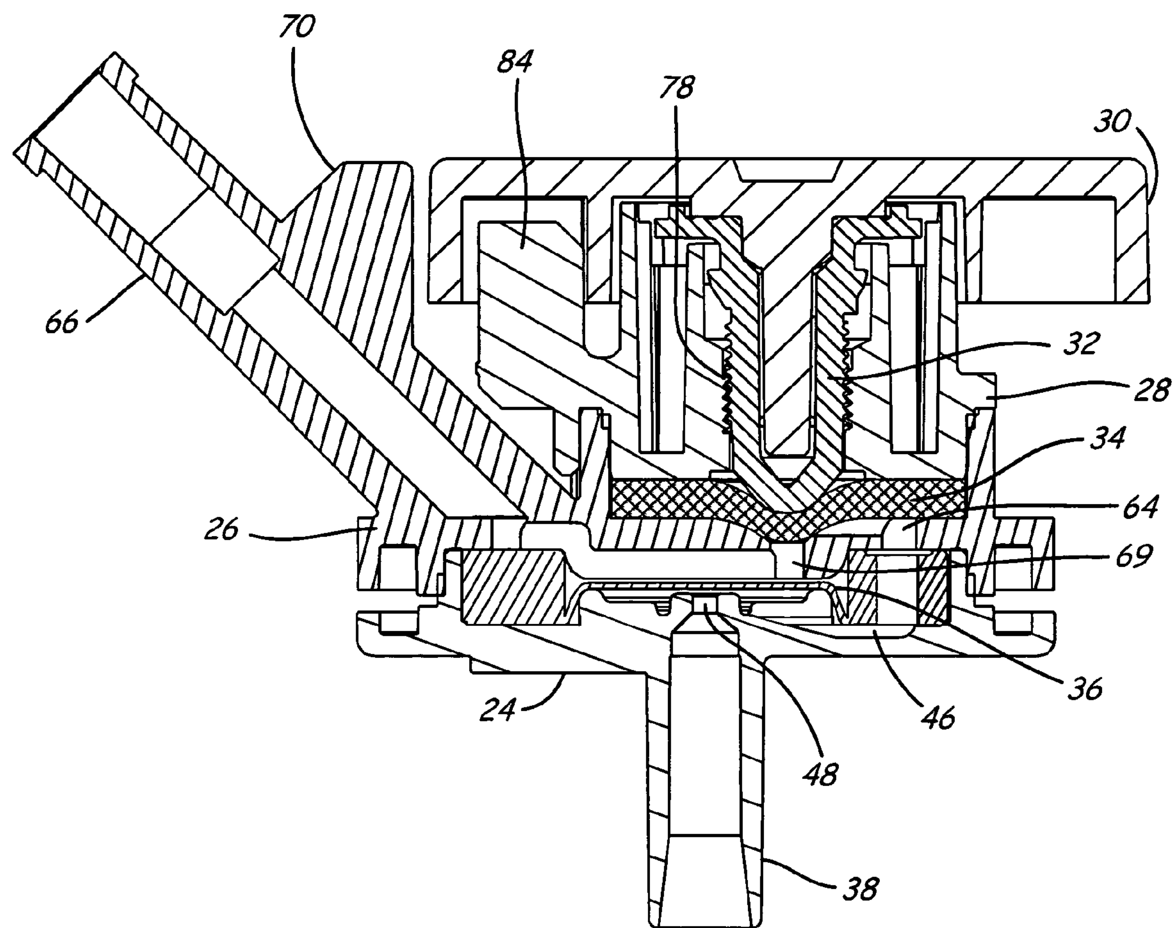
FIG. 8 is a cross section of the flow rate regulator from FIG. 2 assembled.

FIG. 8 is a cross section of flow rate regulator 12 from FIG. 2 assembled. Depicted and labeled in FIG. 8 are components of flow rate regulator 12: lower housing 24, middle housing 26, upper housing 28, screw 32, dial 30, flow control disk 34, flow control membrane 36, outlet 38, lower orifice 48, orifice 64, inlet 66, metering port 69, fin 70, bore 78, and arm 84. Also depicted, but not individually labeled, are many of the sub-components of flow control regulator 12 discussed above. The components of flow rate regulator 12 function to control flow rate and compensate for changes in fluid pressure within IV administration system 10.

Fluid enters flow rate regulator 12 through inlet 66 of middle housing 26. Inlet 66 directs fluid through middle housing 26 to metering port 69. If dial 30 is turned such that screw 32 is advanced sufficiently into upper bore 81 and bore 78 of upper housing 28, then screw 32 will press downwards on flow control disk 34. Under such mechanical pressure, flow control disk 34 deforms and closes off metering port 69 within middle housing 26 thereby slowing the movement of fluid through metering port 69, V-channel 65 and orifice 64. Taken to the extreme, dial 30 can be rotated into an off position where arm 84 of upper housing 28 engages a stop on dial 30 and screw 32 whereby flow control disk 34 closes off metering port 69 and no fluid can pass through. Conversely, dial 30, when attached to screw 32 can be rotated such that screw 32 rotates away from flow control disk 34 incrementally to reduce obstruction of metering port 69 and increase the rate of fluid flow. FIG. 8 depicts flow rate regulator 12 with dial 30 in a full off position such that screw 32 exerts pressure on flow control disk 34 to block metering port 69. When dial 30 is rotated so that screw 32 moves upward and reduces deflection of disk 34, fluid will then flow through flow regulator 12. Fluid exiting middle housing 26 through orifice 64 enters lower housing 24.

Within lower housing 24, fluid is directed via channel 46 radially to lower orifice 48 where flexible membrane 36 is encountered. The space located between flexible membrane 36 and lower orifice 48 varies in response to pressure located on either side of flexible membrane 36. A top surface of flexible membrane 36 is at essentially the same pressure as IV bag 14 and a bottom surface of flexible membrane 36 is at a pressure essentially the same as venipuncture site 20. Therefore, a decrease in head pressure results in reduced top pressure relative to bottom pressure forcing flexible membrane 36 away from port ring 49 and orifice 48 of lower housing 24. When flexible membrane 36 moves away from lower housing it effectively increases opening of lower orifice 48, thereby increasing rate of fluid flow. The converse is also true such that an increase in head pressure results in a more obstructed lower orifice 48 and a decreased rate of fluid flow. After passing through lower orifice 48, fluid exits lower housing 24. Flow rate regulator 12 uses flexible membrane 36 to compensate for changes in pressure and maintain the flow rate chosen by manipulation of dial 30 and screw 32 cooperating with flow control disk 34.

Robust, high volume production of an accurate pressure compensating flow control regulator has proved to be extremely challenging. An important discovery has been the need for extremely accurate centering, concentricity and coaxial alignment of numerous sub-components that are separately produced using high volume multi-cavity tooling. Described above are design features that allow for the manufacturing of a highly accurate flow control regulator using high volume molding and automated assembly. A dial having a stem which couples with a cavity within a screw is one of several cooperative features that allows for robust manufacturability. In addition, these cooperative features allow for precise centering and coaxial alignment of the sub-components used in order to establish and maintain the accurate flow settings during and after the manufacturing process is completed. The centering and coaxial alignment of the sub-components described above utilize various features such as, but not limited to crush bumps, crush ribs, tabs, flow channels, and locating pins. The coaxial alignment of these sub-components along the central axis of metering port 69 allows deflection of flow control disk 34 in a predictable and consistent manner that allows for accurate and reproducible mass production of a flow controller. Although the present invention has been described with reference to preferred embodiments, workers skilled in the art will recognize that changes may be made in form and detail without departing from the spirit and scope of the invention.

The invention claimed is:

1. An IV flow rate regulator comprising:

a housing having an inlet for receiving liquid, an outlet for discharging liquid, a metering port located between the inlet and the outlet, and a threaded bore coaxially aligned with the metering port;

a flow control disk located within the housing above the metering port;

a screw threaded into the bore and extending into the housing to cooperate with the flow control disk, wherein the screw comprises a head, an elongated body that extends downward from the head, external helical threads on an outer surface of the elongated body for engaging internal helical threads in the bore, and a lower end portion that includes a taper and a tip for engaging and deforming the flow control disk;

a dial adhesively bonded to the screw for rotating the screw to depress the flow control disk and thereby establish a flow rate at the metering port; and a plurality of alignment elements for coaxially aligning the housing, the screw, and the dial along a central axis of the metering port, wherein the alignment elements include a cavity centrally located within the screw for receiving and mating with a stem extending centrally from a bottom surface of the dial, the stem including a plurality of radial projections that engage walls of the cavity to self-center the stem and the dial with respect to the screw, and wherein the screw further comprises a circular flange below the head and above the external helical threads with crush features that engage an upper portion of the bore, and wherein the bore includes a lower portion below the internal helical threads with crush features that are engaged by the lower end portion of the screw.

2. The IV flow rate regulator of claim 1, wherein the alignment elements further comprise a plurality of crush features protruding from the housing.

3. The IV flow rate regulator of claim 2, wherein the housing is defined by an upper housing, a middle housing, and a lower housing.

4. The IV flow rate regulator of claim 3, wherein the plurality of crush features are located on the middle housing and deformed by the upper housing during assembly.

5. The IV flow rate regulator of claim 3, wherein the plurality of crush features are located on the middle housing and deformed by the lower housing during assembly.

6. The IV flow rate regulator of claim 3 wherein:

the middle housing includes a fin positioned adjacent the dial;

the upper housing includes an arm having a rib aligned with the fin; and the dial includes an element that engages the rib when the screw is in an off position in which the flow control disk blocks flow of liquid through the metering port.

7. An IV flow rate regulator comprising:

a housing having an inlet for receiving liquid, an outlet for discharging liquid, a metering port located between the inlet and the outlet, and a bore above and coaxially aligned with the metering port, the bore having internal helical threads;

a flow control disk located within the housing above the metering port;

a screw having a head, an elongated body that extends downward from the head, external helical threads on an outer surface of the elongated body for engaging the internal helical threads of the bore, a lower end portion of the elongated body, having a taper and a tip for engaging and deforming the flow control disk, and a cavity extending axially along a center of the elongated body from the head toward the tip, flow channels in a top surface of the head of the screw extending around an opening to the cavity, and an upstanding rib on the top surface of the head extending around the flow channels, the screw extending downward in the bore into the housing to cooperate with the flow control disk; and a dial having a stem extending downward from the dial, a pad on a bottom surface of the dial surrounding an upper end of the stem, and ribs protruding from the upper end of the stem adjacent the pad, the ribs configured to mate with an upper portion of the cavity in the screw, the stem and the ribs received by and mating with the screw cavity such that the dial and the screw are coaxially aligned with one another, wherein the dial rotates the screw to depress the flow control disk and establish a rate of flow at the metering port, wherein the stem is centered on and extending from a bottom surface of the dial, and wherein the dial and the screw are bonded together by adhesive located in the screw cavity, in the flow channels, and between the pad and the top surface of the head bounded by the upstanding rib.

8. The IV flow rate regulator of claim 7, wherein the screw further comprises a circular flange below the head and above the external helical threads with crush features that engage an upper portion of the bore, and wherein the bore includes a lower portion with crush features that are engaged by the lower end portion of the screw.

9. An IV flow rate regulator comprising:

a housing comprising:

an upper housing section having a bore with internal helical threads;

a middle housing section having an inlet for receiving liquid and a metering port; and a lower housing section having an outlet for discharging liquid;

a flow control disk located between the middle housing and the upper housing, the flow control disk centered above the metering port;

a screw extending through the bore to cooperate with the flow control disk, wherein the screw comprises a head, an elongated body that extends downward from the head, external helical threads on an outer surface of the elongated body for engaging internal helical threads in the bore, and a lower end portion that includes a taper and a tip for engaging and deforming the flow control disk;

a dial capable of rotating the screw to depress the flow control disk and establish a flow rate at the metering port; and crush features located between the upper housing and the middle housing, between the middle housing and the lower housing, and between the screw and a wall of the upper housing defining the bore, for coaxially aligning the bore, screw, and dial of the IV flow control regulator about a central axis defined by the metering port, wherein the crush features are deformed during assembly of the IV flow control regulator, and wherein the crush features include:

crush bumps located on the screw between the head and the external helical threads and deformed by a portion of a wall defining the bore of the upper housing located above the internal helical threads;

crush ribs located within the bore of the upper housing below the internal helical threads and deformed by a portion of the lower end portion of the screw located between the external helical threads and the taper;

a first set of crush ribs located on a top side of the middle housing and deformed by the upper housing; and a second set of crush ribs located on a bottom side of the middle housing and deformed by the lower housing.

10. The IV flow rate regulator of claim 9 wherein:

the middle housing includes a fin positioned adjacent the dial;

the upper housing includes an arm having a rib aligned with the fin; and the dial includes an element that engages the rib when the screw is in an off position in which the flow control disk blocks flow of liquid through the metering port.

* * * * *